(12) United States Patent
Eberle et al.

(10) Patent No.: US 6,365,620 B2
(45) Date of Patent: Apr. 2, 2002

(54) TRIFLUOROMETHYLPYRROLCARBOX-AMIDES

(75) Inventors: Martin Eberle, Bottmingen; Harald Walter, Rodersdorf, both of (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/780,897

(22) Filed: Feb. 9, 2001

Related U.S. Application Data

(63) Continuation of application No. PCT/EP99/05837, filed on Aug. 10, 1999.

(30) Foreign Application Priority Data

Aug. 12, 1998 (GB) ............................... 9817548

(51) Int. Cl.$^7$ ................... C07D 207/40; C07D 409/12; C07D 409/14; A01N 43/36
(52) U.S. Cl. ................... 514/422; 548/537; 514/423; 549/59
(58) Field of Search ................ 548/537; 549/59; 514/422, 423

(56) References Cited

U.S. PATENT DOCUMENTS

| | | | |
|---|---|---|---|
| 5,045,554 A | * 9/1991 | Alt et al. | 514/365 |
| 5,330,995 A | * 7/1994 | Eicken et al. | 514/355 |
| 5,438,070 A | * 8/1995 | Eicken et al. | 514/403 |
| 5,589,493 A | * 12/1996 | Eicken et al. | 514/355 |
| 5,998,450 A | * 12/1999 | Eicken et al. | 514/355 |

* cited by examiner

Primary Examiner—Floyd D. Higel
Assistant Examiner—Kamal Saeed
(74) Attorney, Agent, or Firm—William A. Teoli, Jr.

(57) ABSTRACT

The invention relates to pesticidal trifluoromethylpyrrolcarboxamides of formula I

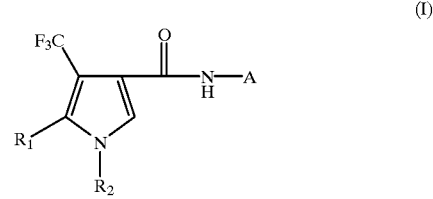

wherein
$R_1$ is hydrogen, halogen, $C_{1-4}$haloalkyl or $C_{1-4}$alkyl,
$R_2$ is $C_{1-4}$alkyl, $C_{1-4}$haloalkyl, $C_{1-4}$alkoxy-$C_{1-4}$alkyl, cyano, $C_{1-4}$alkylsulfonyl, phenylsulfonyl, di($C_{1-4}$alkyl)aminosulfonyl, $C_{1-6}$alkylcarbonyl, benzoyl, or substituted phenylsulfonyl or benzoyl, and
A is a group

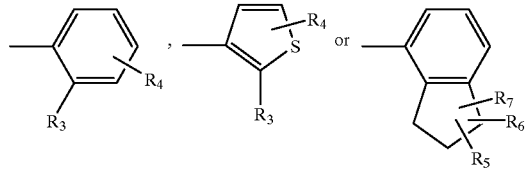

wherein
$R_3$ is $C_{1-6}$alkyl, $C_{1-6}$haloalkyl, $C_{2-6}$alkenyl, $C_{2-6}$haloalkenyl, $C_{2-6}$alkinyl, $C_{1-6}$alkoxy, $C_{1-6}$haloalkoxy, $C_{2-6}$alkenyloxy, $C_{2-6}$haloalkenyloxy, $C_{2-6}$alkinyloxy, $C_{3-7}$cycloalkyl, $C_{1-4}$alkyl-$C_{3-7}$cycloalkyl, $C_{4-7}$cycloalkenyl, $C_{1-4}$alkyl-$C_{4-7}$cycloalkenyl, $C_{3-7}$cycloalkyloxy, $C_{1-4}$alkyl-$C_{3-7}$cycloalkyloxy, $C_{5-7}$cycloalkenyloxy, $C_{1-4}$alkyl-$C_{5-7}$cycloalkenyloxy, phenyl, naphthyl, phenoxy, naphthyloxy, or substituted phenyl or phenoxy wherein the substitutents are one to three groups independently selected from halogen, $C_{1-4}$alkyl, $C_{1-4}$alkoxy, $C_{1-4}$alkylthio, cyano, $C_{1-4}$alkoxycarbonyl, $C_{1-4}$alkylcarbonyl, $C_{1-4}$haloalkyl, $C_{1-4}$haloalkoxy, methylenedioxy or difluoromethylenedioxy, or phenyl;
$R_4$ is hydrogen, halogen, $C_{1-4}$alkyl, $C_{1-4}$haloalkyl, $C_{1-4}$alkoxy or $C_{1-4}$haloalkoxy; and
$R_5$, $R_6$ and $R_7$ independently of each other are $C_{1-6}$alkyl, $C_{3-7}$cycloalkyl or $C_{3-7}$cycloalkyl-$C_{2-14}$alkyl.

The compounds have plant-protecting properties and are suitable for protecting plants against infestation by phytopathogenic microorganisms.

11 Claims, No Drawings

TRIFLUOROMETHYLPYRROLCARBOX-AMIDES

This is a continuation of international application no. PCT/EP99/05837, filed Aug. 10, 1999, the contents of which are fully incorporated by reference herein.

The present invention relates to novel trifluoromethylpyrrolcarboxamides which have microbicidal activity, in particular fungicidal activity. The invention also relates to the preparation of these substances, to agrochemical compositions which comprise at least one of the novel compounds as active ingredient, to the preparation of the compositions mentioned and to the use of the active ingredients or compositions in agriculture and horticulture for controlling or preventing infestation of plants by phytopathogenic microorganisms, preferably fungi.

The trifluoromethylpyrrolcarboxamides of the present invention have the general formula I

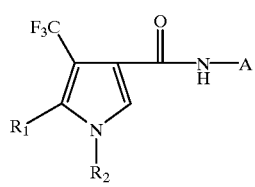

(I)

wherein $R_1$ is hydrogen, halogen, $C_{1-4}$haloalkyl or $C_{1-4}$alkyl, $R_2$ is $C_{1-4}$alkyl, $C_{1-4}$haloalkyl, $C_{1-4}$alkoxy-$C_{1-4}$alkyl, cyano, $C_{1-4}$alkylsulfonyl, phenylsulfonyl, di($C_{1-4}$alkyl)aminosulfonyl, $C_{1-6}$alkylcarbonyl, benzoyl, or substituted phenylsulfonyl or benzoyl, and A is a group

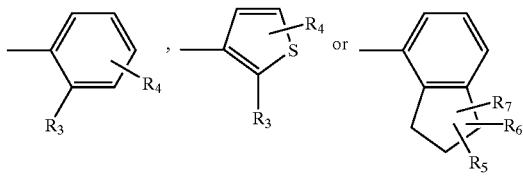

wherein $R_3$ is $C_{1-6}$alkyl, $C_{1-6}$haloalkyl, $C_{2-6}$alkenyl, $C_{2-6}$haloalkenyl, $C_{2-6}$alkinyl, $C_{1-6}$alkoxy, $C_{1-6}$haloalkoxy, $C_{2-6}$alkenyloxy, $C_{2-6}$haloalkenyloxy, $C_26$alkinyloxy, $C_{3-7}$cycloalkyl, $C_{1-4}$alkyl-$C_{3-7}$cycloalkyl, $C_{4-7}$cycloalkenyl, $C_{1-4}$alkyl-$C_{4-7}$cycloalkenyl, $C_{3-7}$cycloalkyloxy, $C_{1-4}$alkyl-$C_{3-7}$cycloalkyloxy, $C_{5-7}$cycloalkenyloxy, $C_{1-4}$alkyl-$C_{5-7}$cycloalkenyloxy, phenyl, naphthyl, phenoxy, naphthyloxy, or substituted phenyl or phenoxy wherein the substitutents are one to three groups independently selected from halogen, $C_{1-4}$alkyl, $C_{1-4}$alkoxy, $C_{1-4}$alkylthio, cyano, $C_{1-4}$alkoxycarbonyl, $C_{1-4}$alkylcarbonyl, $C_{1-4}$haloalkyl, $C_{1-4}$haloalkoxy, methylenedioxy or difluoromethylenedioxy, or phenyl;

$R_4$ is hydrogen, halogen, $C_{1-4}$alkyl, $C_{1-4}$haloalkyl, $C_{1-4}$alkoxy or $C_{1-4}$haloalkoxy; and $R_5$, $R_6$ and $R_7$ independently of each other are $C_{1-6}$alkyl, $C_{3-7}$cycloalkyl or $C_{3-7}$cycloalkyl-$C_4$alkyl.

Nicotinic acid amides with fungicidal properties useful in agricultural practice are known from EP-A-0545099. The disclosed compounds for practical purposes do not always satisfy the needs of the modern agriculture.

Surprisingly, it has now been found that the compounds of formula I exhibit improved biological properties which render them more suitable for the practical use in agriculture and horticulture.

Where asymmetrical carbon atoms are present in the compounds of formula I these compounds are in optically active form. The invention relates to the pure isomers, such as enantiomers and diastereomers, as well as to all possible mixtures of isomers, e.g. mixtures of diastereomers, racemates or mixtures of racemates.

Within the present specification alkyl denotes methyl, ethyl, n-propyl, isopropyl, n-butyl, sec-butyl, isobutyl, tert-butyl, n-pentyl, iso-pentyl, sec-pentyl, tert-pentyl, and neo-pentyl. Non-branched alkyl is preferred. Alkyl as part of other radicals such as alkoxy, alkylthio, haloalkyl, alkylcycloalkyl, alkylcycloalkoxy, alkylcarbonyl, alkylsulfonyl, alkylamino, etc. is understood in an analogous way. Halogen will be understood generally as meaning fluoro, chloro, bromo or iodo. Fluoro, chloro or bromo are preferred meanings. Halogen as part of other radicals such as haloalkyl, haloalkoxy, haloalkenyl, haloalkenyloxy or halophenyl, etc. is understood in an analogous way. Substituents of the substituted phenylsulfonyl and benzoyl may be present mono- to five times and are preferably independently selected from halogen, $C_{1-4}$alkyl, $C_{1-4}$alkoxy, $C_{1-4}$alkylthio, cyano, $C_{1-4}$alkoxycarbonyl, $C_{1-4}$alkylcarbonyl, $C_{1-4}$haloalkyl, $C_{1-4}$haloalkoxy, methylenedioxy or difluoromethylenedioxy, or phenyl. Where phenyl groups as parts of phenyl, phenylsulfonyl, phenoxy and benzoyl are substituted such radicals for example designate 2-chlorophenyl, 3-chlorophenyl, 4-chlorophenyl, 2-fluorophenyl, 3-fluorophenyl, 4-fluorophenyl, 2,4-dichlorophenyl, 3,4-dichlorophenyl, 3,5-dichlorophenyl, 2,4-difluorophenyl, 3,4-difluorophenyl, 3,5-difluorophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 4-methylphenyl, 4-ethylphenyl, 4-isopropylphenyl 4-tert.butylphenyl, 3,4-dimethylphenyl, 2,4,6-trimethylphenyl, 3-chloro-4-fluorophenyl, 4-chloro-3-fluorophenyl, 4-biphenyl, 3-biphenyl, and the like.

A special subgroup of active ingredients is represented by those compounds of formula I
wherein $R_1$ is hydrogen or $C_{1-4}$alkyl, $R_2$ is $C_{1-4}$alkyl, and A is a group

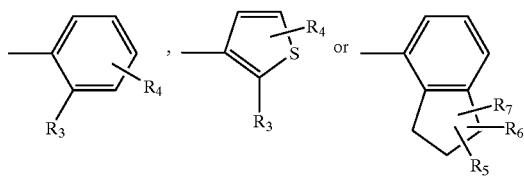

wherein $R_3$ $C_{1-6}$alkyl, $C_{1-6}$haloalkyl, $C_{2-6}$alkenyl, $C_{2-6}$haloalkenyl, $C_{2-6}$alkinyl, $C_{1-6}$alkoxy, $C_{1-6}$haloalkoxy, $C_{2-6}$alkenyloxy, $C_{2-6}$haloalkenyloxy, $C_{2-6}$alkinyloxy, $C_{3-7}$cycloalkyl $C_{1-4}$alkyl-$C_{3-7}$cycloalkyl, $C_{4-7}$cycloalkenyl, $C_{1-4}$alkyl-$C_{4-7}$cycloalkenyl, $C_{3-7}$cycloalkyl, $C_{1-4}$alkyl-$C_{3-7}$cycloalkyloxy, $C_{5-7}$cycloalkenyloxy, $C_{1-4}$alkyl-$C_{5-7}$cycloalkenyloxy, phenyl, naphthyl, phenyl substituted by one to three groups independently selected from halogen, $C_{1-4}$alkyl, $C_{1-4}$alkoxy, $C_{1-4}$alkylthio, cyano, $C_{1-4}$alkoxycarbonyl, $C_{1-4}$alkylcarbonyl, $C_{1-4}$haloalkyl, $C_{1-4}$haloalkoxy, methylenedioxy or difluoromethylenedioxy, or phenyl;

$R_4$ is hydrogen, halogen or $C_{1-4}$alkyl; and $R_5$, $R_6$ and $R_7$ independently of each other are $C_{1-6}$alkyl, $C_{3-7}$cycloalkyl or $C_{3-7}$cycloalkyl-$C_{1-4}$alkyl.

Within the group of compounds of formula I those compounds are preferred wherein:

a) $R_1$ is hydrogen or methyl, or b) $R_2$ is methyl, or c) $R_3$ is phenyl or phenyl substituted with halogen.

Another preferred subgroup is constituted by the compounds of formula I wherein $R_1$ is hydrogen or methyl, $R_2$ is methyl, and $R_3$ is phenyl or phenyl substituted with halogen.

Preferred individual compounds are:

N-(2-biphenylyl)-1-methyl-4-trifluoromethylpyrrol-3-carboxamide,

N-(4'-chloro-2-biphenylyl)-4-trifluoromethylpyrrol-3-carboxamide,

N-(4'-fluoro-2-biphenylyl)-4-trifluoromethylpyrrol-3-carboxamide,

N-[2-(4-fluorophenyl)-3-thienyl)-4-trifluoromethylpyrrol-3-carboxamide,

N-[2-(4-chlorophenyl)-3-thienyl)-4-trifluoromethylpyrrol-3-carboxamide,

N-(3',4'-difluoro-2-biphenylyl)-4-trifluoromethylpyrrol-3-carboxamide,

N-(3'-trifluoromethyl-2-biphenylyl)-4-trifluoromethylpyrrol-3-carboxamide, and

N-(4'-chloro-3'-fluoro-2-biphenylyl)-4-trifluoromethylpyrrol-3-carboxamide.

The compounds according to formula I may be prepared according to the following reaction scheme 1.

Scheme 1

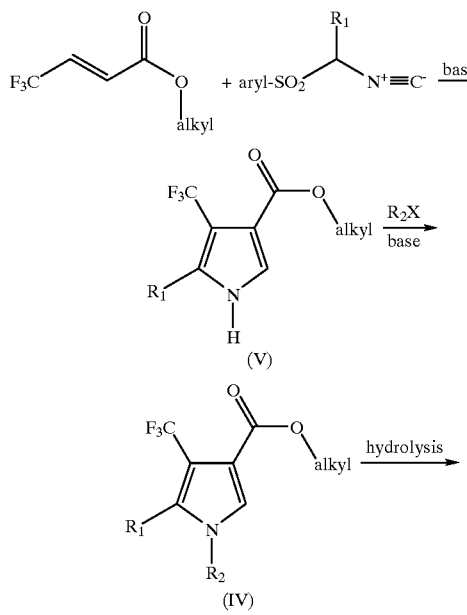

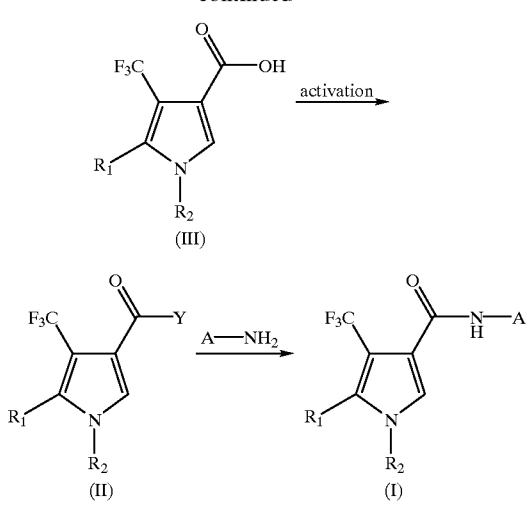

wherein A, $R_1$ and $R_2$ are as defined for formula I, X and Y are leaving groups, alkyl designates a lower alkyl moiety, and aryl stands for phenyl or tolyl.

The leaving groups X and Y preferably designate halogen atoms, but may also stand for moieties of mixed anhydrides, e.g. —O—CO-alkyl, —O—PO(alkyl)$_2$, —O—C(=N-alkyl), triazolyl, and the like.

Alternatively the introduction of the radicals $R_2$ and A may be a different order according to scheme 2.

Scheme 2

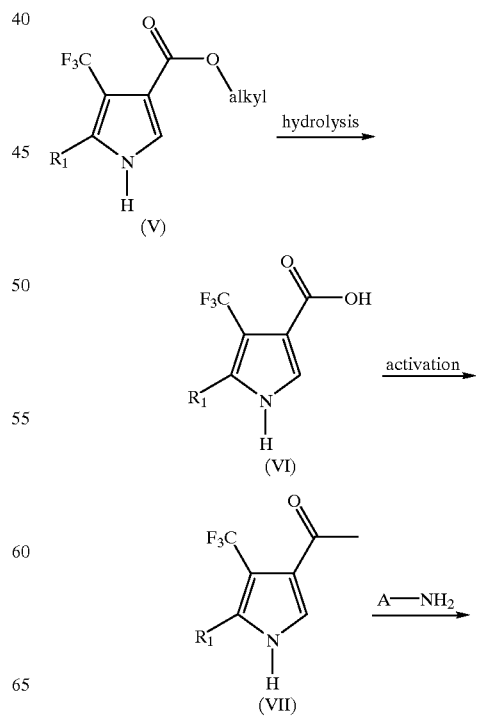

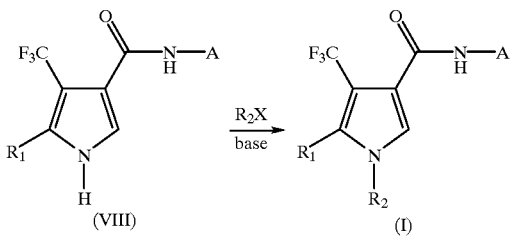

wherein A, $R_1$, $R_2$, X and Y are as defined for scheme 1

In special cases of substitution patterns it may be favourable to utilize a protective group at the 1-position of the pyrrol ring in order to avoid side reactions during the amidation reaction at the carbonyl function in 3-position. Suitable protective groups are benzyl and the like. Also introduction and cleaving of the protective group is done by common benzylation and hydrolysation reactions.

The new carboxamides of formula I are preferably obtained by reacting an activated carboxylic acid of formula II with an aromatic amine. Depending on the leaving group Y the reaction is run in the presence of an acid binding agent. Inert solvents are preferably used, but also aqueous solvent mixtures, referred to as Schotten-Baumann conditions, may be employed.

Activation is achieved by reacting the pyrrol carboxylic acid III with an activating agent such acid halide, such as thionyl chloride or oxalyl chloride, to give the corresponding acyl chloride (Y=chlorine) or by any other general coupling activation method known in the literature.

The carboxylic acids of formula III may be prepared from the corresponding esters by hydrolysis using standard hydrolysis conditions.

The N-alkylation of pyrrol carboxylic esters of formula V to give the N-alkylated pyrrol carboxylic esters of formula IV may be achieved by reacting a pyrrol carboxylic ester of formula V with an alkylating agent, such as a dialkylsulfate, an alkyl halogenide or a alkylsulfonate using standard conditions. The pyrrol carboxylic esters of formula V may typically be prepared according to the van Leusen protocol, i.e. the reaction of an alkyl acrylate with an aryl sulfonyl isocyanide in the presence of a base. Typical bases employed in scheme 1 include metal hydrides, metal alcoholates and metal hydroxides. Any solvent which is inert under the reaction conditions may be used. Representative solvents include ethers (diethylether, dimethoxyethane, THF and the like), polar aprotic solvents, such as DMSO, DMF, DMA, or protic solvents, such as alcohols. Also mixtures of such solvents may be used. In many cases phase transfer reaction conditions are applicable which naturally require a two-phase reaction system. Preferably the entire reaction sequence of scheme 1 is conducted as a single-vessel-reaction.

Surprisingly, it has now been found that the novel compounds of formula I have, for practical purposes, a very advantageous spectrum of activities for protecting plants against diseases that are caused by fungi as well as by bacteria and viruses.

The compounds of formula I can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic micro-organisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

The compounds I are, for example, effective against the phytopathogenic fungi of the following classes: Fungi imperfecti (e.g. Botrytis, Pyricularia, Helminthosporium, Fusarium, Septoria, Cercospora and Alternaria) and Basidiomycetes (e.g. Rhizoctonia, Hemileia, Puccinia). Additionally, they are also effective against the Ascomycetes classes (e.g. Venturia and Erysiphe, Podosphaera, Monilinia, Uncinula) and of the Oomycetes classes (e.g. Phytophthora, Pythium, Plasmopara). Outstanding activity has been observed against powdery mildew (Erysiphe spp.). Furthermore, the novel compounds of formula I are effective against phytopathogenic bacteria and viruses (e.g. against Xanthomonas spp, Pseudomonas spp, Erwinia amylovora as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinache, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilisers, antifoams, viscosity regulators, binders or tackifiers as well as fertilisers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilisers. Such carriers are for example described in WO 97/33890.

The compounds of formula I are normally used in the form of compositions and can be applied to the crop area or plant to be treated, simultaneously or in succession with further compounds. These further compounds can be e.g. fertilisers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2-[(2-trifluoromethyl)-pyrid-6-yloxymethyl]-3-methoxyacrylate or 2-[α{[(α-methyl-3-trifluoromethyl-benzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur,triazoxide, tricyclazole, triforine, validamycin, (S)-5-methyl-2-methylthio-5-phenyl-3-phenyl-amino-3,5-dihydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfonamide (IKF-916), N-(1-cyano-1,2-dimethylpropyl)-2-(2,4-dichlorophenoxy)-propionamide (AC 382042), or iprovalicarb (SZX 722).

A preferred method of applying a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

The agrochemical formulations will usually contain from 0.1 to 99% by weight, preferably from 0.1 to 95% by weight, of the compound of formula 1, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail. Temperatures are given in degrees Celsius. The following abbreviations are used: m.p.=melting point; b.p.=boiling point. "NMR" means nuclear magnetic resonance spectrum. MS stands for mass spectrum. "%" is percent by weight, unless corresponding concentrations are indicated in other units.

PREPARATION EXAMPLES

Example P 1

N-(2-biphenylyl)-1-methyl-4-trifluoromethylpyrrol-3-carboxamide a) 1-Methyl-4-trifluoromethylpyrrol-3-carboxylic acid

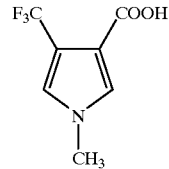

Sodium hydride (8.0 g of a 75% dispersion in oil) is suspended at +5° C. in a mixture of DMSO (300 ml) and diethylether (100 ml). A solution of ethyl 4,4,4-trifluorocrotonate (20 g) and TOSMIC (23 g) in DMSO (100 ml) is added through a dropping funnel at such a rate that the temperature does not exceed 10° C. After stirring the reaction mixture for an additional hour at room temperature methyl iodide (15.6 ml) is added with cooling. After 2 hours at room temperature the reaction mixture is poured onto crushed ice. Repeated extraction with ether, washing of the combined organic phases with brine and evaporation of the solvent under reduced pressure gives a product mixture in form of a light amber oil. The crude product mixture is heated at 60° C. in a mixture of ethanol (100 ml) and sodium hydroxide (50 ml of a 30% aqueous solution). Washing of the solution with ether, acidifying of the aqueous phase with concentrated hydrochloric acid and filtering gives the 1-methyl-4-trifluoromethylpyrrol-3-carboxylic acid in form of a crystalline solid.

$^1$H-NMR(CDCl$_3$): 7.24(d, 1H); 6.88(d, 1H); 3.63 (s,3H).

b) N-(2-biphenylyl)-1-methyl-4-trifluoromethylpyrrol-3-carboxamide

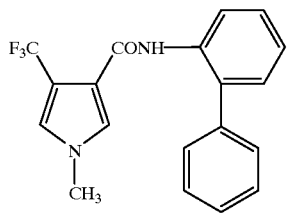

A solution of 1-methyl-4-trifluoromethylpyrrol-3-carboxylic acid (1.9 g) and oxalyl chloride (0.9 ml) in methylene chloride (20 ml) is stirred at room temperature in the presence of a catalytic amount of DMF. The solvent is evaporated under reduced pressure to give a crystalline solid. This solid is dissolved in methylene chloride (1 ml) and added to a solution of 2-biphenylamine (1.7 g) and triethylamine ( 4.2 ml) in methylene chloride (20 ml) at 0° C. The reaction mixture is stirred at room temperature for 2 hours. Evaporation of the solvent under reduced pressure, addition of water and filtering gives the N-(2-biphenylyl)-1-methyl-4-trifluoromethylpyrrol-3-carboxamide.

$^1$H-NMR(CDCl$_3$): 8.37(d,1H); 7.60(s,br, 1H); 7.48–7.14 (m,8H); 7.03(d, 1H); 6.88(s,3H).

Example P 2

N-(2-biphenylyl)-1,5-dimethyl-4-trifluoromethylpyrrol-3-carboxamide a) 1,5-Dimethyl-4-trifluoromethylpyrrol-3-carboxylic acid

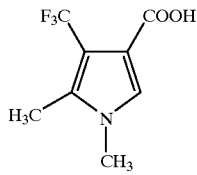

A mixture of TOSMIC (20 g), methyliodide (18.5 g) and N-benzyl triethylammonium chloride (1 g) in methylene chloride (100 ml) and aqueous sodium hydroxide (30 ml of a 50% solution) are stirred at 5° C. for 3 hours. A solution of ethyl 4,4,4-trifluorocrotonate (20 g) in methylene chloride (50 ml) is added through a dropping funnel at such a rate that the temperature does not exceed 25° C. After stirring the reaction mixture for an additional hour at room temperature excess methyl iodide is added with cooling. After 2 hours at room temperature the reaction mixture is poured onto crushed ice. Repeated extraction with ether, washing of the combined organic phases with brine and evaporation of the solvent gives the crude product mixture. The pure intermediate is obtained after chromatography on silicagel. Hydrolysis is achieved under the conditions mentioned under example 1 a) to give the 1,5-dimethyl-4-trifluoromethylpyrrol-3-carboxylic acid in form of a colorless crystalline solid.

$^1$H-NMR (d$_6$-DMSO): 12.04 (s,br,1H); 7.50(s,1H); 3.58 (s,3H); 2.27 (s,3H).

b) N-(2-biphenylyl)-1,5-dimethyl-4-trifluoromethylpyrrol-3-carboxamide

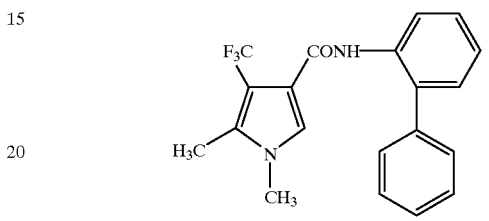

A solution of 1,5-dimethyl-4-trifluoromethylpyrrol-3-carboxylic acid (1.9 g) and oxalyl chloride (0.9 ml) in methylene chloride (20 ml) is stirred at room temperature in the presence of a catalytic amount of DMF. The solvent is evaporated under reduced pressure to give a crystalline solid. This solid is dissolved in methylene chloride (1 ml) and added to a solution of 2-biphenylamine (1.7 g) and triethylamine (4.2 ml) in methylene chloride (20 ml) at 0° C. The reaction mixture is stirred at room temperature for 2 hours. Evaporation of the solvent under reduced pressure, addition of water and filtering gives the N-(2-biphenylyl)-1,5-dimethyl-4-trifluoromethylpyrrol-3-carboxamide.

$^1$H-NMR(CDCl$_3$): 8.39(d,1H); 7.58(s,br,1H); 7.48–7.14 (m,9H); 3.58 (s,3H); 2.27

The following compounds are prepared in a similar way, using analogous methods.

Table 1: Compounds of formula I wherein R$_1$ is hydrogen, R$_2$ is methyl and A corresponds to one line in the Table A.

Table 2: Compounds of formula I wherein R$_1$ and R$_2$ are methyl and A corresponds to one line in the Table A.

Table 3: Compounds of formula I wherein R$_2$ is hydrogen, R$_2$ is ethyl and A corresponds to one line in the Table A.

Table 4: Compounds of formula I wherein R$_1$ is hydrogen, R$_2$ is methoxymethyl and A corresponds to one line in the Table A.

Table 5: Compounds of formula I wherein R$_1$ is hydrogen, R$_2$ is cyano and A corresponds to one line in the Table A.

Table 6: Compounds of formula I wherein R$_1$ is hydrogen, R$_2$ is methylsulfonyl and A corresponds one line in the Table A.

Table 7: Compounds of formula I wherein R$_1$ is hydrogen, R$_2$ is phenylsulfonyl and A corresponds to one line in the Table A.

Table 8: Compounds of formula I wherein R$_1$ is hydrogen, R$_2$ is acetyl and A corresponds to one line in the Table A.

Table 9: Compounds of formula I wherein R$_1$ is hydrogen, R$_2$ is methoxyacetyl and A corresponds one line in the Table A.

Table 10: Compounds of formula I wherein R$_1$ is hydrogen, R$_2$ is benzoyl and A corresponds one line in the Table A.

Table 11: Compounds of formula I wherein $R_1$ is hydrogen, $R_2$ is 4-fluorobenzoyl and A corresponds to one line in the Table A.
TABLE A
| Comp. No. | A |
|---|---|
| 01 | 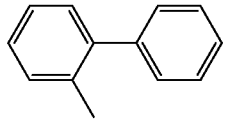 |
| 02 | 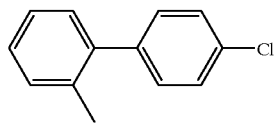 |
| 03 | 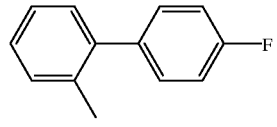 |
| 04 | 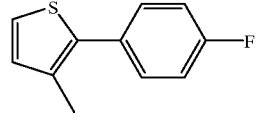 |
| 05 | 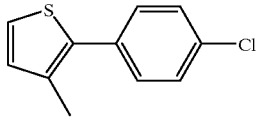 |
| 06 | 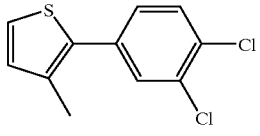 |
| 07 | 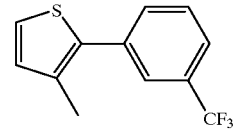 |
| 08 | 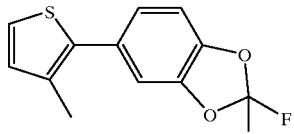 |
| 09 | 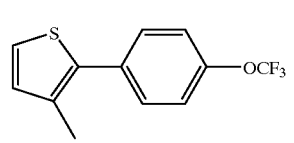 |
TABLE A-continued
| Comp. No. | A |
|---|---|
| 10 | 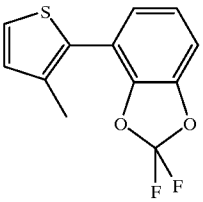 |
| 11 | 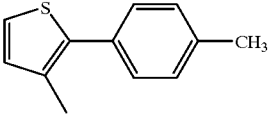 |
| 12 | 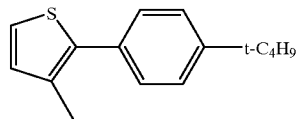 |
| 13 | 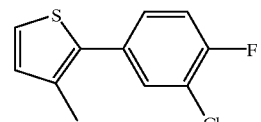 |
| 14 | 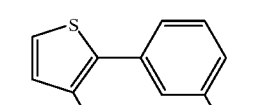 |
| 15 | 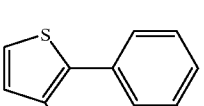 |
| 16 | 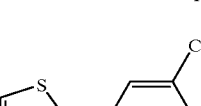 |
| 17 | 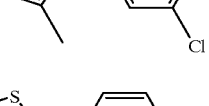 |
| 18 | 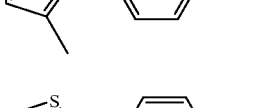 |
| 19 | 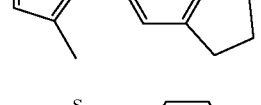 |

TABLE A-continued
| Comp. No. | A |
|---|---|
| 20 | 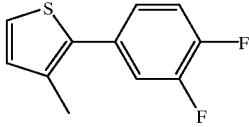 |
| 21 | 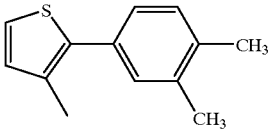 |
| 22 | 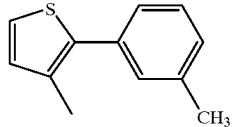 |
| 23 | 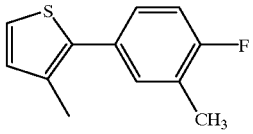 |
| 24 | 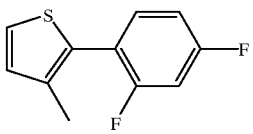 |
| 25 | 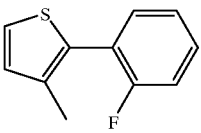 |
| 26 | 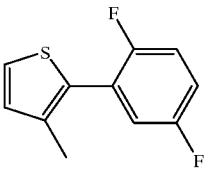 |
| 27 | 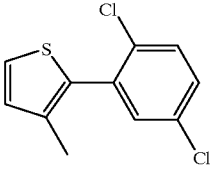 |
| 28 | 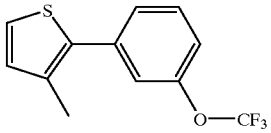 |
| 29 | 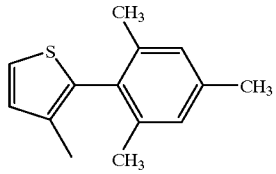 |
| 30 | 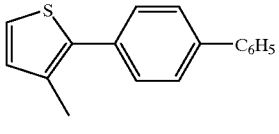 |
| 31 | 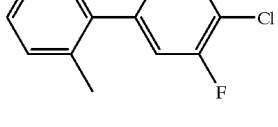 |
| 32 | 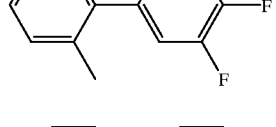 |
| 33 | 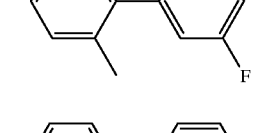 |
| 34 | 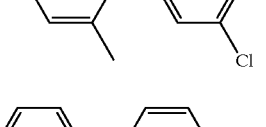 |
| 35 |  |
| 36 | 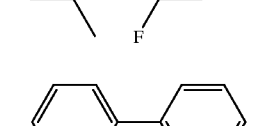 |
| 37 | 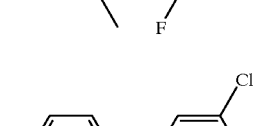 |
| 38 | 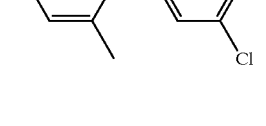 |

TABLE A-continued
| Comp. No. | A |
|---|---|
| 39 | 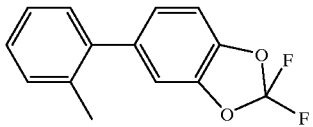 |
| 40 | 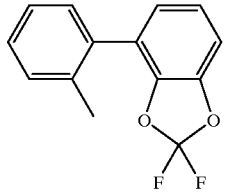 |
| 41 | 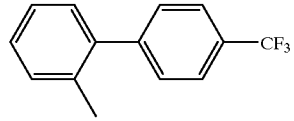 |
| 42 | 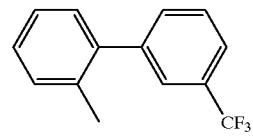 |
| 43 | 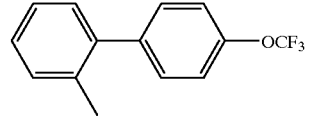 |
| 44 | 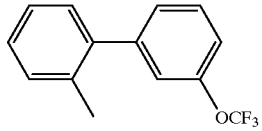 |
| 45 | 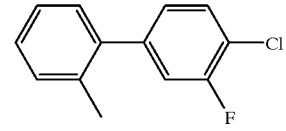 |
| 46 | 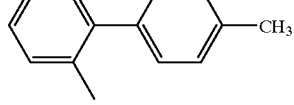 |
| 47 | 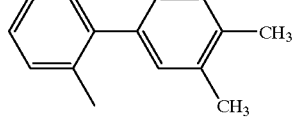 |
| 48 | 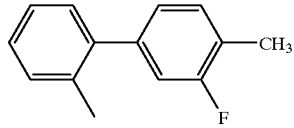 |
| 49 | 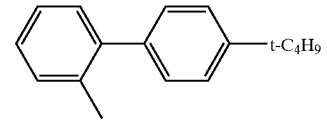 |
| 50 | 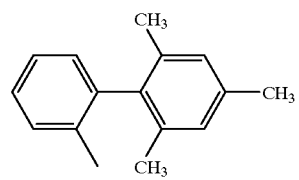 |
| 51 | 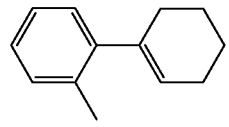 |
| 52 | 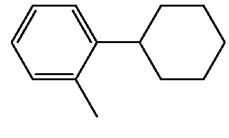 |
| 53 | 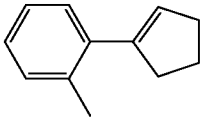 |
| 54 | 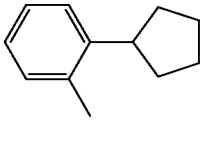 |
| 55 | 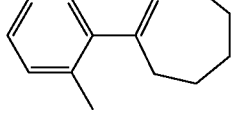 |
| 56 | 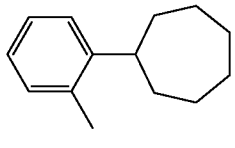 |
| 57 | 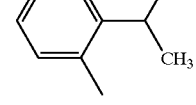 |
| 58 | 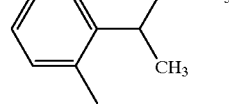 |

TABLE A-continued
| Comp. No. | A |
|---|---|
| 59 | 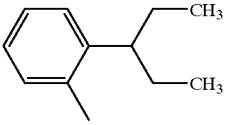 |
| 60 | 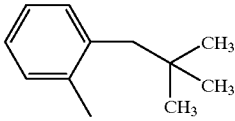 |
| 61 | 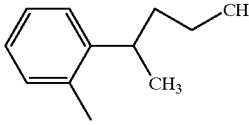 |
| 62 | 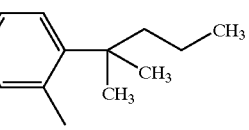 |
| 63 | 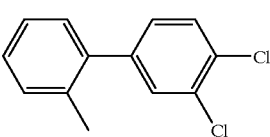 |
| 64 | 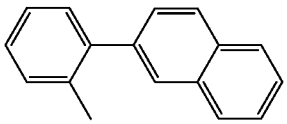 |
| 65 | 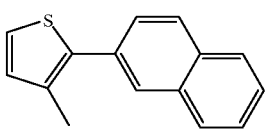 |
| 66 | 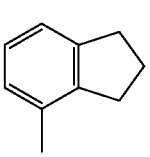 |
| 67 | 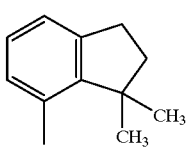 |
| 68 | 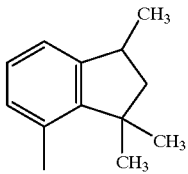 |
| 69 | 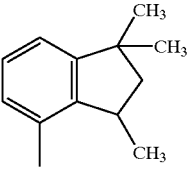 |
| 70 | 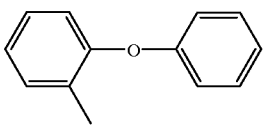 |
| 71 | 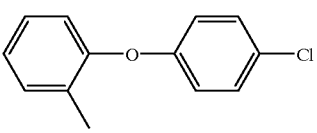 |
| 72 | 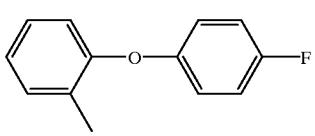 |
| 73 | 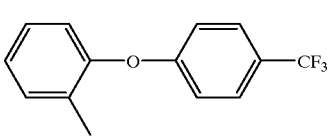 |
| 74 | 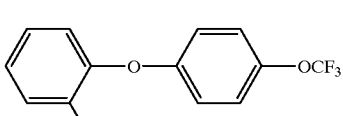 |
| 75 | 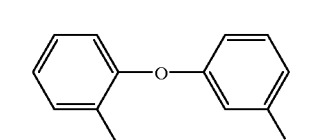 |
| 76 | 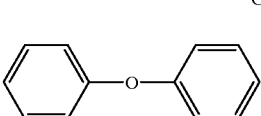 |
Table 12 Physico-chemical data for selected compounds of the preceding tables 1 to 11
TABLE 12
Physico-chemical data for selected compounds of the preceding tables 1 to 11
| Comp. No. | physico-chemical data m.p. [° C.] or $^1$H-NMR (CDCl$_3$) |
|---|---|
| 1.01 | 8.37(d, 1H); 7.60(s, br, 1H); 7.48–7.14(m, 8H); 7.03(s, 1H); 6.88(s, 1H); 3.63(s, 3H); m.p. 100–102. |

TABLE 12-continued

Physico-chemical data for selected compounds of the preceding tables 1 to 11

| Comp. No. | physico-chemical data m.p. [° C.] or $^1$H-NMR (CDCl$_3$) |
|---|---|
| 1.02 | 8.27(D, 1H); 7.50(S, br, 1H); 7.46–7.18(m, 7H); 7.10(d, 1H); 6.88(s, 1H); 3.63(s, 3H). |
| 1.03 | 8.30(d, 1H); 7.52(s, br, 1H); 7.44–7.12(m, 8H; 6.88(s, 1H); 3.63(s, 3H); m.p. 151–153. |
| 1.04 | 7.85(d, 1H); 7.74(s, br, 1H); 7.44(dd, 2H); 7.30(s, 1H); 7.28(s, 1H); 7.13(dd, 2H); 6.93(s, 1H); 3.68(s, 3H); m.p. 127–129. |
| 1.05 | 7.84(d, 1H); 7.74(s, br, 1H); 7.49(s, 4H); 7.30(d, 1H); 7,28(d, 1H); 6.96(d, 1H); 3.68(s, 3H; m.p. 142–145. |
| 1.30 | 7.89(d, 1H); 7.76–7.25(m, 12H); 6.95(s, 1H); 3.69(s, 3H); m.p. 168–169. |
| 1.35 | m.p. 160–161. |
| 1.38 | 8.25(d, 1H); 7.50(s, br, 1H); 7.45–7.08(m, 7H); 6.68(s, 1H); 3,65(s, 3H); resin. |
| 1.40 | m.p. 122–123. |
| 1.42 | m.p. 142–143. |
| 1.71 | m.p. 63–65. |
| 1.72 | m.p. 112–114. |
| 1.76 | resin |
| 2.02 | m.p. 163–165. |
| 2.03 | resin |
| 2.05 | resin |
| 2.35 | m.p. 124–125. |
| 2.71 | resin |
| 3.01 | resin |
| 3.02 | resin |
| 3.03 | resin |
| 3.71 | resin |
| 4.02 | resin |
| 4.03 | resin |
| 4.71 | resin |
| 5.02 | resin |
| 5.03 | resin |
| 5.71 | resin |
| 8.02 | resin |
| 8.03 | resin |
| 8.04 | resin |
| 8.05 | resin |
| 8.71 | resin |

Formulation Examples for Compounds of Formula I

Working procedures for preparing formulations of the compounds of formula I such as Emulsifiable concentrates, Solutions, Granulates, Dusts and Wettable powders are described in WO 97/33890.

BIOLOGICAL EXAMPLES

Fungicidal Actions

Example B-1

Action Against *Puccinia recondita*/Wheat (Brownrust on Wheat)

1 week old wheat plants cv. Arina are treated with the formulated test compound (0.02% active ingredient) in a spray chamber. One day after application wheat plants are inoculated by spraying a spore suspension ($1\times10^5$ uredospores/ml) on the test plants. After an incubation period of 2 days at 20° C. and 95% r. h. plants are kept in a greenhouse for 8 days at 20° C. and 60% r.h. The disease incidence is assessed 10 days after inoculation. Compounds of Tables 1 to 11 show good activity in these tests (<20% infestation).

Example B-2

Action Against *Podosphaera leucotricha*/Apple (Powdery Mildew on Apple)

5 week old apple seedlings cv. McIntosh are treated with the formulated test compound (0.002% active ingredient) in a spray chamber. One day after application apple plants are inoculated by shaking plants infected with apple powdery mildew above the test plants. After an incubation period of 12 days at 22° C. and 60% r. h. under a light regime of 14/10 h (light/dark) the disease incidence is assessed.

Compounds of Tables 1 to 11 show good activity in this test. The compounds 1.01, 1.02, 1.03, 1.04, 1.05, 1.30, 1.35. 1.38, 1.39, 1.40, 1.42, 1.71, 1.72, 1.76, 2.02, 2.03, 2.05, 2.35, 2.71, 3.01, 3.02, 3.03, 3.71, 4.02, 4.03, 4.71, 5.02, 5.03, 5.71, 8.02, 8.03, 8.04 and 8.71 exhibit strong efficacy (<20% infestation).

Example B-3

Action Against *Venturia inaequalis*/Apple (Scab on Apple)

4 week old apple seedlings cv. McIntosh are treated with the formulated test compound (0.02% active ingredient) in a spray chamber. One day after application apple plants are inoculated by spraying a spore suspension ($4\times10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Compounds of Tables 1 to 11 show good activity in this test. The compounds 1.01, 1.02, 1.03, 1.04, 1.05, 1.30, 1.35. 1.38, 1.39, 1.40, 1.42, 1.71, 1.72, 1.76, 2.02, 2.03, 2.05, 2.35, 2.71, 3.01, 3.02, 3.03, 3.71, 4.02, 4.03, 4.71, 5.02, 5.03, 5.71, 8.02, 8.03, 8.04 and 8.71 exhibit strong efficacy (<20% infestation).

Example B-4

Action Against *Erysiphe graminis*/Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r.h. in a greenhouse the disease incidence is assessed.

Compounds of Tables 1 to 11 show good activity in this test. The compounds 1.01, 1.02, 1.03, 1.04, 1.05, 1.30, 1.35. 1.38, 1.39, 1.40, 1.42, 1.71, 1.72, 1.76, 2.02, 2.03, 2.05, 2.35, 2.71, 3.01, 3.02, 3.03, 3.71, 4.02, 4.03, 4.71, 5.02, 5.03, 5.71, 8.02, 8.03, 8.04 and 8.71 exhibit strong efficacy (<20% infestation).

Example B-5

Action Against *Botrytis Cinerea*/Apple (Botrytis on Apple Fruits)

In an apple fruit cv. Golden Delicious 3 holes are drilled and each filled with 30 µl droplets of the formulated test compound (0.002% active ingredient). Two hours after application 50 µl of a spore suspension of *B. cinerea* ($4\times10^5$ conidia/ml) are pipetted on the application sites. After an incubation period of 7 days at 22° C. in a growth chamber the disease incidence is assessed.

Compounds of Tables 1 to 11 show good activity in this test. The compounds 1.01, 1.02, 1.03, 1.04, 1.05, 1.30, 1.35. 1.38, 1.39, 1.40, 1.42, 1.71, 1.72, 1.76, 2.02, 2.03, 2.05, 2.35, 2.71, 3.01, 3.02, 3.03, 3.71, 4.02, 4.03, 4.71, 5.02, 5.03, 5.71, 8.02, 8.03, 8.04 and 8.71 exhibit very strong efficacy (<10% infestation).

Example B-6

Action Against *Botrytis Cinerea*/Grape (Botrytis on Grapes)

5 week old grape seedlings cv. Gutedel are treated with the formulated test compound (0.002% active ingredient) in a spray chamber. Two days after application grape plants are inoculated by spraying a spore suspension ($1 \times 10^6$ conidia/ml) on the test plants. After an incubation period of 4 days at 21° C. and 95% r.h. in a greenhouse the disease incidence is assessed.

Compounds of Tables 1 to 11 show good activity in this test. The compounds 1.01, 1.02, 1.03, 1.04, 1.05, 1.30, 1.35. 1.38, 1.39, 1.40, 1.42, 1.71, 1.72, 1.76, 2.02, 2.03, 2.05, 2.35, 2.71, 3.01, 3.02, 3.03, 3.71, 4.02, 4.03, 4.71, 5.02, 5.03, 5.71, 8.02, 8.03, 8.04 and 8.71 exhibit very strong efficacy (<10% infestation).

Example B-7

Action Against *Botrytis cinerea*/Tomato (Botrytis on Tomatoes)

4 week old tomato plants cv. Roter Gnom are treated with the formulated test compound (0.002% active ingredient) in a spray chamber. Two days after application tomato plants are inoculated by spraying a spore suspension ($1 \times 10^5$ conidia/ml) on the test plants. After an incubation period of 4 days at 20° C. and 95% r.h. in a growth chamber the disease incidence is assessed.

Compounds of Tables 1 to 11 show good activity in this test. The compounds 1.01, 1.02, 1.03, 1.04, 1.05, 1.30, 1.35. 1.38, 1.39, 1.40, 1.42, 1.71, 1.72, 1.76, 2.02, 2.03, 2.05, 2.35, 2.71, 3.01, 3.02, 3.03, 3.71, 4.02, 4.03, 4.71, 5.02, 5.03, 5.71, 8.02, 8.03, 8.04 and 8.71 exhibit very strong efficacy (<10% infestation).

Example B-8

Action Against *Pyrenophora teres*/Barley (Net Blotch on Barley)

1 week old barley plants cv. Express are treated with the formulated test compound (0.002% active ingredient) in a spray chamber. Two days after application barley plants are inoculated by spraying a spore suspension ($3 \times 10^4$ conidia/ml) on the test plants. After an incubation period of 2 days at 20° C. and 95% r.h. plants are kept for 2 days at 20° C. and 60% r.h. in a greenhouse. The disease incidence is assessed 4 days after inoculation.

Compounds of Tables 1 to 11 show good activity in this test. The compounds 1.01, 1.02, 1.03, 1.04, 1.05, 1.30, 1.35. 1.38, 1.39, 1.40, 1.42, 1.71, 1.72, 1.76, 2.02, 2.03, 2.05, 2.35, 2.71, 3.01, 3.02, 3.03, 3.71, 4.02, 4.03, 4.71, 5.02, 5.03, 5.71, 8.02, 8.03, 8.04 and 8.71 exhibit strong efficacy (<20% infestation).

Example B-9

Action Against *Septoria nodorum*/Wheat (Septoria Leaf Spot on Wheat)

1 week old wheat plants cv. Arina are treated with the formulated test compound (0.02% active ingredient) in a spray chamber. One day after application wheat plants are inoculated by spraying a spore suspension ($5 \times 10^5$ conidia/ml) on the test plants. After an incubation period of 1 day at 20° C. and 95% r.h. plants are kept for 10 days at 20° C. and 60% r.h. in a greenhouse. The disease incidence is assessed 11 days after inoculation.

Compounds of Tables 1 to 11 show good activity in this test. The compounds 1.01, 1.02, 1.03, 1.04, 1.05, 1.30, 1.35. 1.38, 1.39, 1.40, 1.42, 1.71, 1.72, 1.76, 2.02, 2.03, 2.05, 2.35, 2.71, 3.01, 3.02, 3.03, 3.71, 4.02, 4.03, 4.71, 5.02, 5.03, 5.71, 8.02, 8.03, 8.04 and 8.71 exhibit strong efficacy (<20% infestation).

What is claimed is:

1. A trifluoromethylpyrrolcarboxamide of formula I

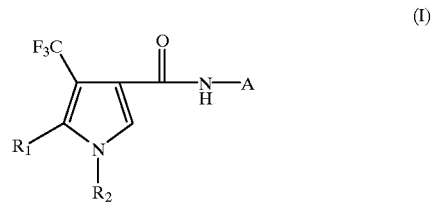

wherein $R_1$ is hydrogen, halogen, $C_{1-4}$haloalkyl or $C_{1-4}$alkyl, $R_2$ is $C_{1-4}$alkyl, $C_{1-4}$haloalkyl, $C_{1-4}$alkoxy-$C_{1-4}$alkyl, cyano, $C_{1-4}$alkylsulfonyl, phenylsulfonyl, di($C_{1-4}$alkyl)aminosulfonyl, $C_{1-6}$alkylcarbonyl, benzoyl, or substituted phenylsulfonyl or benzoyl, and A is a group

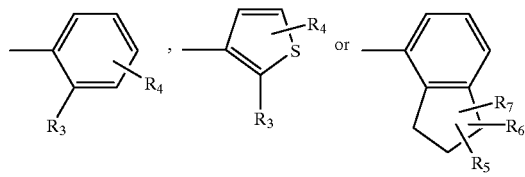

wherein $R_3$ is $C_{1-6}$alkyl, $C_{1-6}$haloalkyl, $C_{2-6}$alkenyl, $C_{2-6}$haloalkenyl, $C_{2-6}$alkinyl, $C_{1-6}$alkoxy, $C_{1-6}$haloalkoxy, $C_{2-6}$alkenyloxy, $C_{2-6}$haloalkenyloxy, $C_{2-6}$alkinyloxy, $C_{3-7}$cycloalkyl, $C_{1-4}$alkyl-$C_{3-7}$cycloalkyl, $C_{4-7}$cycloalkenyl, $C_{1-4}$alkyl-$C_{4-7}$cycloalkenyl, $C_{3-7}$cycloalkyloxy, $C_{1-4}$alkyl-$C_{3-7}$cycloalkyloxy, $C_{5-7}$cycloalkenyloxy, $C_{1-4}$alkyl-$C_{5-7}$cycloalkenyloxy, phenyl, naphthyl, phenoxy, naphthyloxy, or substituted phenyl or phenoxy wherein the substitutents are one to three groups independently selected from halogen, $C_{1-4}$alkyl, $C_{1-4}$alkoxy, $C_{1-4}$alkylthio, cyano, $C_{1-4}$alkoxycarbonyl, $C_{1-4}$alkylcarbonyl, $C_{1-4}$haloalkyl, $C_{1-4}$haloalkoxy, methylenedioxy or difluoromethylenedioxy, or phenyl;

$R_4$ is hydrogen, halogen, $C_{1-4}$alkyl, $C_{1-4}$haloalkyl, $C_{1-4}$alkoxy or $C_{1-4}$haloalkoxy; and $R_5$, $R_6$ and $R_7$ independently of each other are $C_{1-6}$alkyl, $C_{3-7}$cycloalkyl or $C_{3-7}$cycloalkyl-$C_{1-4}$alkyl.

2. Compounds of formula I according to claim 1 wherein $R_1$ is hydrogen or $C_{1-4}$alkyl, $R_2$ is $C_{1-4}$alkyl, and A is a group

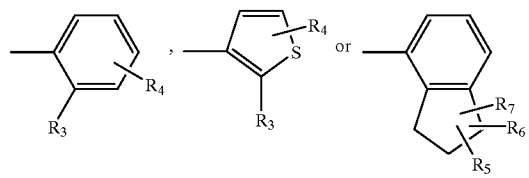

wherein

R$_3$ is C$_{1-6}$alkyl, C$_{1-6}$haloalkyl, C$_{2-6}$alkenyl, C$_{2-6}$haloalkenyl, C$_{2-6}$alkinyl, C$_{1-6}$alkoxy, C$_{1-6}$haloalkoxy, C$_{2-6}$alkenyloxy, C$_{2-6}$haloalkenyloxy, C$_{2-6}$alkinyloxy, C$_{3-7}$cycloalkyl, C$_4$alkyl-C$_{3-7}$cycloalkyl, C$_{4-7}$cycloalkenyl, C$_{1-4}$alkyl-C$_{4-7}$cycloalkenyl, C$_{3-6}$cycloalkyloxy, C$_{1-4}$alkyl-C$_{3-7}$cycloalkyloxy, C$_{5-7}$cycloalkenyloxy, C$_{1-4}$alkyl-C$_{5-7}$cycloalkenyloxy, phenyl, naphthyl, phenyl substituted by one to three groups independently selected from halogen, C$_{1-4}$alkyl, C$_{1-4}$alkoxy, C$_{1-4}$alkylthio, cyano, C$_{1-4}$alkoxycarbonyl, C$_{1-4}$alkylcarbonyl, C$_{1-4}$haloalkyl, C$_{1-4}$haloalkoxy, methylenedioxy or difluoromethylenedioxy, or phenyl;

R$_4$ is hydrogen, halogen or C$_{1-4}$alkyl; and

R$_5$, R$_6$ and R$_7$ independently of each other are C$_{1-6}$alkyl, C$_{3-7}$cycloalkyl or C$_{3-7}$cycloalkyl-C$_{1-4}$alkyl.

3. A compound according to claim 1 wherein R$_1$ is hydrogen or methyl.

4. A compound according to claim 1 wherein R$_2$ is methyl.

5. A compound according to claim 1 wherein R$_3$ is phenyl or phenyl substituted with halogen.

6. A compound according to claim 1 wherein R$_1$ is hydrogen or methyl, R$_2$ is methyl, and R$_3$ is phenyl or phenyl substituted with halogen.

7. A compound according to claim 1 selected from the group comprising

N-(2-biphenylyl)-1-methyl-4-trifluoromethylpyrrol-3-carboxamide,

N-(4'-chloro-2-biphenylyl)-4-trifluoromethylpyrrol-3-carboxamide,

N-(4'-fluoro-2-biphenylyl)-4-trifluoromethylpyrrol-3-carboxamide,

N-[2-(4-fluorophenyl)-3-thienyl]-4-trifluoromethylpyrrol-3-carboxamide,

N-[2-(4-chlorophenyl)-3-thienyl]-4-trifluoromethylpyrrol-3-carboxamide,

N-(3',4'-difluoro-2-biphenylyl)-4-trifluoromethylpyrrol-3-carboxamide,

N-(3'-trifluoromethyl-2-biphenylyl)-4-trifluoromethylpyrrol-3-carboxamide, and

N-(4'-chloro-3'-fluoro-2-biphenylyl)-4-trifluoromethylpyrrol-3-carboxamide.

8. A process for the preparation of compounds of formula I which comprises reacting the starting materials according to the scheme

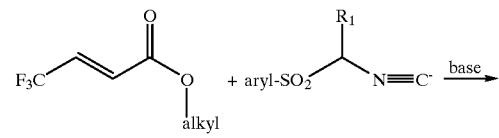

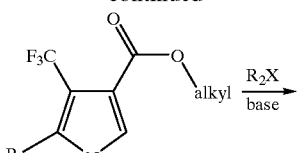

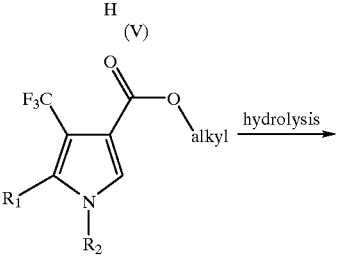

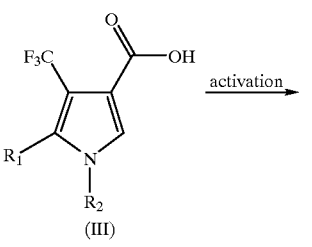

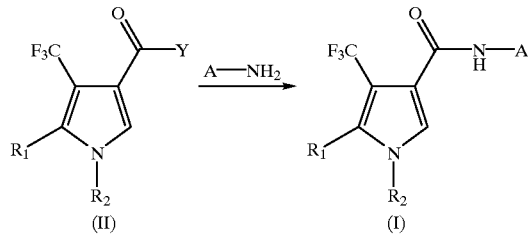

wherein A, R$_1$ and R$_2$ are as defined for formula I in claim 1, X and Y are leaving groups, alkyl designates a lower alkyl moiety, and aryl stands for phenyl or tolyl.

9. A process for the preparation of compounds of formula I which comprises reacting the starting materials according to the scheme

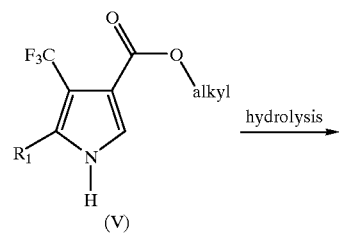

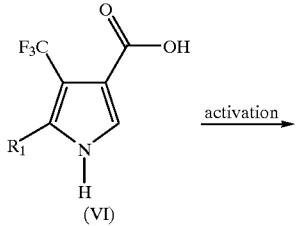

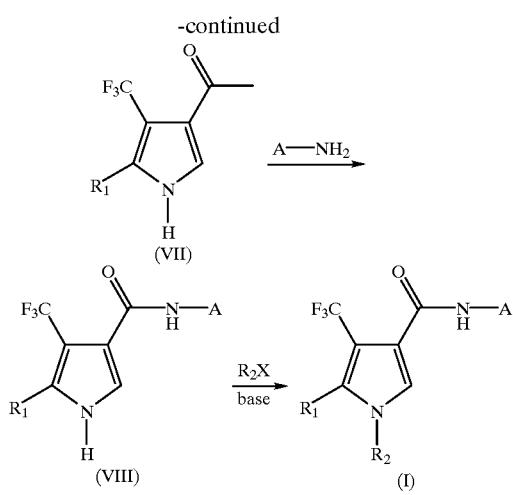

wherein A, $R_1$ and $R_2$ are as defined for formula I in claim 1, X and Y are leaving groups, and alkyl designates a lower alkyl moiety, optionally with the utilization of a protective group during the amidation step.

10. A composition for controlling microorganisms and preventing attack and infestation of plants therewith, wherein the active ingredient is a compound as claimed in claim 1 together with a suitable carrier.

11. A method of controlling or preventing infestation of cultivated plants by phytopathogenic microorganisms by application of a compound of formula I as claimed in claim 1 to plants, to parts thereof or to the locus thereof.

* * * * *